United States Patent
Zhang et al.

(10) Patent No.: US 10,525,166 B2
(45) Date of Patent: Jan. 7, 2020

(54) SELENIUM-DOPED HYDROXYAPATITE AND PREPARATION METHOD THEREOF

(71) Applicant: HUAZHONG UNIVERSITY OF SCIENCE AND TECHNOLOGY, Hubei (CN)

(72) Inventors: Shengmin Zhang, Hubei (CN); Yan Li, Hubei (CN); Hang Hao, Hubei (CN)

(73) Assignee: HUAZHONG UNIVERSITY OF SCIENCE AND TECHNOLOGY, Hubei (CN)

(*) Notice: Subject to any disclaimer, the term of this patent is extended or adjusted under 35 U.S.C. 154(b) by 10 days.

(21) Appl. No.: 15/889,235

(22) Filed: Feb. 6, 2018

(65) Prior Publication Data
US 2019/0167848 A1 Jun. 6, 2019

(30) Foreign Application Priority Data
Dec. 1, 2017 (CN) .......................... 2017 1 1249751

(51) Int. Cl.
*A61L 27/50* (2006.01)
*A61L 27/42* (2006.01)
(Continued)

(52) U.S. Cl.
CPC ............... *A61L 27/50* (2013.01); *A61L 27/16* (2013.01); *A61L 27/425* (2013.01);
(Continued)

(58) Field of Classification Search
None
See application file for complete search history.

(56) References Cited

U.S. PATENT DOCUMENTS

| | | | |
|---|---|---|---|
| 2008/0206554 A1* | 8/2008 | Riman | A61L 27/32 428/330 |
| 2011/0091510 A1* | 4/2011 | Lele | B82Y 30/00 424/400 |

FOREIGN PATENT DOCUMENTS

| | | |
|---|---|---|
| CN | 102249206 | 11/2011 |
| CN | 106063947 | 11/2016 |

OTHER PUBLICATIONS

Zhang et al. (CN102249206 English translation) (Year: 2011).*
(Continued)

*Primary Examiner* — Aradhana Sasan
*Assistant Examiner* — Quanglong N Truong
(74) *Attorney, Agent, or Firm* — JCIPRNET (57) ABSTRACT

The invention relates to a selenium-doped hydroxyapatite and a preparation method thereof. The selenium-doped hydroxyapatite provided is a single crystal comprising a rod-like structure, a uniform morphology, and a good dispersibility. The preparation method comprises adding a mixed solution of a phosphate and a selenite dropwise to a mixed solution of a calcium salt and a dispersing agent, and reacting for 1.5-2.5 hrs at a controlled temperature of 80-90° C., to obtain a solution of a calcium phosphate amorphous precursor, followed by performing a hydrothermal reaction at 190-210° C., to obtain a selenium-doped hydroxyapatite comprising a rod-like structure. Compared with selenium-doped hydroxyapatite with severe agglomeration, the selenium-doped hydroxyapatite provided in the present invention comprises good dispersibility and able to have better prevention of clogging problem in human body when in use, thus having a good prospect using as a multi-functional new material for bone repair in patients as a repair material for bone defects, an anti-tumor, etc.

5 Claims, 5 Drawing Sheets

(51) Int. Cl.
*A61L 27/16* (2006.01)
*C01B 25/32* (2006.01)

(52) U.S. Cl.
CPC ........ *C01B 25/327* (2013.01); *C01P 2002/54* (2013.01); *C01P 2002/70* (2013.01); *C01P 2002/72* (2013.01); *C01P 2002/82* (2013.01); *C01P 2004/03* (2013.01); *C01P 2004/04* (2013.01); *C01P 2004/16* (2013.01)

(56) References Cited

OTHER PUBLICATIONS

Dunfeng et al. (CN106063947 English translation) (Year: 2016).*
Abinaya Rajendran, et al., "Crystalline selenite substituted carbonated hydroxyapatite nanorods: Synthesis, characterization, evaluation of bioactivity and cytotoxicity," International Journal of Applied Ceramic Technology, vol. 14, Jan. 2017, pp. 68-76.

\* cited by examiner

SELENIUM-DOPED HYDROXYAPATITE AND PREPARATION METHOD THEREOF

CROSS-REFERENCE TO RELATED APPLICATION

This application claims the priority benefit of China application serial no. 201711249751.7, filed on Dec. 1, 2017. The entirety of the above-mentioned patent application is hereby incorporated by reference herein and made a part of this specification.

BACKGROUND OF THE INVENTION

1. Field of the Invention

The present invention relates to the technical field of biomaterials, and particularly to a selenium-doped hydroxyapatite and a preparation method thereof.

2. Description of Related Art

Hydroxyapatite is a main inorganic component in human bone and teeth, which has good biocompatibility, osteoconductivity, and biological activity, and thus is an ideal bone repair material and bone filler material. In addition, studies have shown that hydroxyapatite modified by doping with ions also has some special biological properties, for example, magnesium-doped hydroxyapatite can be used as a gene carrier, silver-doped hydroxyapatite can be used as an efficient effective and broad-spectrum antibacterial agent with slow release.

Selenium is one of the trace elements essential for human and animal life. The selenium element has anti-tumor, anti-bacterial, and anti-aging effects, and can improve human immunity. Selenium uptake plays an important role in bone formation. Therefore, it is of great significance to prepare a multi-functional new bone repair material having good osteoconductivity, and anti-tumor, anti-bacterial and other effects by incorporating selenium into hydroxyapatite. However, there are very few studies concerning selenium-doped hydroxyapatite. Patent CN 102249206 A discloses a selenium-doped hydroxyapatite and a preparation method thereof. The hydroxyapatite prepared through the method is a nano-sized selenium-doped hydroxyapatite having poor dispersibility and severe agglomeration. Patent CN 106063947 A discloses a method for preparing a selenium-doped nano-hydroxyapatite. The method uses a relatively complex system; and the prepared hydroxyapatite is also a nano-sized selenium-doped hydroxyapatite, and no large-size hydroxyapatite can be prepared.

SUMMARY OF THE INVENTION

In view of the above problems, the present invention provides a selenium-doped hydroxyapatite having a good dispersibility with a relatively larger size, and a preparation method thereof. The method is feasible and simple, and the selenium-doped hydroxyapatite provided is a single crystal having a good dispersibility with a relatively larger size reaching micrometer scale.

To achieve the above object, the following technical solutions are adopted in the present invention.

A selenium-doped hydroxyapatite is provided, which is a single crystal having a rod-like structure, a uniform morphology, and a good dispersibility.

Further, the selenium-doped hydroxyapatite has a diameter ranging from 30 nm to 300 nm and a length ranging from 500 nm to 2 μm.

Further, a molar substitution of selenium for phosphorous in the selenium-doped hydroxyapatite is 0.01-10%.

A method for preparing a selenium-doped hydroxyapatite comprises adding a mixed solution of a phosphate and a selenite dropwise to a mixed solution of a calcium salt and a dispersing agent, and reacting for 1.5-2.5 hrs at a controlled temperature of 80-90° C., to obtain a solution of a calcium phosphate amorphous precursor, followed by performing a hydrothermal reaction at 190-210° C., to obtain the selenium-doped hydroxyapatite having a rod-like structure.

In the method, the hydrothermal reaction time is 12-24 hrs.

In the method, the method for preparing a selenium-doped hydroxyapatite comprises specifically:

(1) adding the mixed solution of the phosphate and the selenite dropwise to the mixed solution of the calcium salt and the dispersing agent, and reacting for 1.5-2.5 hrs at pH 9-10 and at a reaction temperature of 80-90° C., to obtain a solution of an amorphous calcium phosphate precursor;

(2) centrifuging the solution of the amorphous calcium phosphate precursor, collecting a precipitate of the solution of the amorphous calcium phosphate precursor, adding anhydrous ethanol, placing in a reactor, and reacting for 12-24 hrs at a temperature maintained at 190-210° C.; and (3) washing the precipitate of the solution of the amorphous calcium phosphate precursor with anhydrous ethanol and water respectively, and centrifuging, to remove the impurity ions in the post-reaction system, and drying, to finally obtain the selenium-doped hydroxyapatite having a rod-like structure.

In the method, a molar substitution of selenium for phosphorous in the selenium-doped hydroxyapatite is 0.01-10%.

In the method for preparing a selenium-doped hydroxyapatite, the molar ratio of the elements calcium, phosphorous and selenium is 1:(0.42-0.58):(0.17-0.006).

Preferably, the calcium salt is calcium nitrate, the phosphate is ammonium dihydrogen phosphate, dibasic sodium phosphate or dibasic ammonium phosphate, and the selenite is sodium selenite.

Preferably, the dispersing agent is sodium polyacrylate.

In the present invention, the mixed solution of the phosphate and the selenite is added dropwise to the mixed solution of the calcium salt and the dispersing agent and reacted for a particular period of time at a controlled temperature, to form a spherical amorphous calcium phosphate precursor, which is then subjected to a hydrothermal reaction to obtain a selenium-doped hydroxyapatite having a rod-like structure and a good dispersibility. The extent of reaction to the amorphous calcium phosphate precursor during the reaction greatly affects the morphology of the subsequent material. If the extent of reaction to the amorphous calcium phosphate precursor is too low, severely agglomerated and granular selenium-doped hydroxyapatite is formed upon hydrothermal reaction. If the extent of reaction to the amorphous calcium phosphate precursor is too high, the shape of the precursor will change from spherical to fusiform-like, the morphology remains fusiform-like after the hydrothermal reaction, and the agglomeration is severe.

The present invention has the following beneficial effects.

The method for preparing a selenium-doped hydroxyapatite provided in the present invention is simple, and the raw materials are readily available. The selenium-doped hydroxyapatite thus provided is a single crystal having a rod-like structure, a uniform morphology, and a good dispersibility, in which the selenium content is 0.01-10%, the diameter is ranging from 30 nm to 300 nm, and the length is ranging from 500 nm to 2 μm. Compared with the selenium-doped hydroxyapatite suffering from severe agglomeration, the selenium-doped hydroxyapatite provided in the present invention has good dispersibility and able to have better prevention of clogging problem in human body when in use, thus having a good prospect using as a multi-functional new material having anti-tumor effect for bone repair in patients as a repair material for bone defects, an antitumor, etc.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Reference will now be made in detail to the present preferred embodiments of the invention, examples of which are illustrated in the accompanying drawings. Wherever possible, the same reference numbers are used in the drawings and the description to refer to the same or like parts.

The present invention will be described in further detail below with reference to specific embodiments and comparative examples. However, the protection scope of the present invention is not limited thereto.

Example 1

By the following preparation method, a hydroxyapatite doped with selenium in an amount of 2% was synthesized. The steps were specifically as follows.

(1) 2.95 g of calcium nitrate was dissolved in 250 mL of water, and 0.93 g of ammonium dihydrogen phosphate and 0.12 g of sodium selenite were dissolved in 250 mL of water, and stirred at room temperature until they were completely dissolved, to obtain a solution of a calcium nitrate and a mixed solution of an ammonium dihydrogen phosphate and a sodium selenite, respectively.

(2) The solution of the calcium nitrate was warmed to a temperature of 85° C. in a constant-temperature magnetic stirrer, and adjusted to pH 9 with aqueous ammonia. 1 mL of a solution of 50% sodium polyacrylate was added dropwise to the solution of the calcium nitrate to obtain a mixed solution of a calcium nitrate and a sodium polyacrylate. The mixed solution of the ammonium dihydrogen phosphate and the sodium selenite was slowly added dropwise to the mixed solution of the calcium nitrate and the sodium polyacrylate, and duration of the dropwise process is 30 min.

(3) The reaction solution was maintained at pH 9 by adding aqueous ammonia dropwise, the temperature was maintained at 85° C. by the constant-temperature magnetic stirrer, and the reaction was continued for 2 hrs.

(4) The reaction solution was centrifuged, and a precipitate, that is, an amorphous calcium phosphate precursor was collected. 50 mL of anhydrous ethanol was added to the precipitate of the amorphous calcium phosphate precursor, transferred to a reactor, sealed, and reacted for 24 hrs at a temperature maintained at 200° C.

(5) After naturally cooling to room temperature, the reactor was opened, and a selenium-doped hydroxyapatite was finally obtained after several rounds of sequential washing with anhydrous ethanol and water, and drying.

Figure 1:
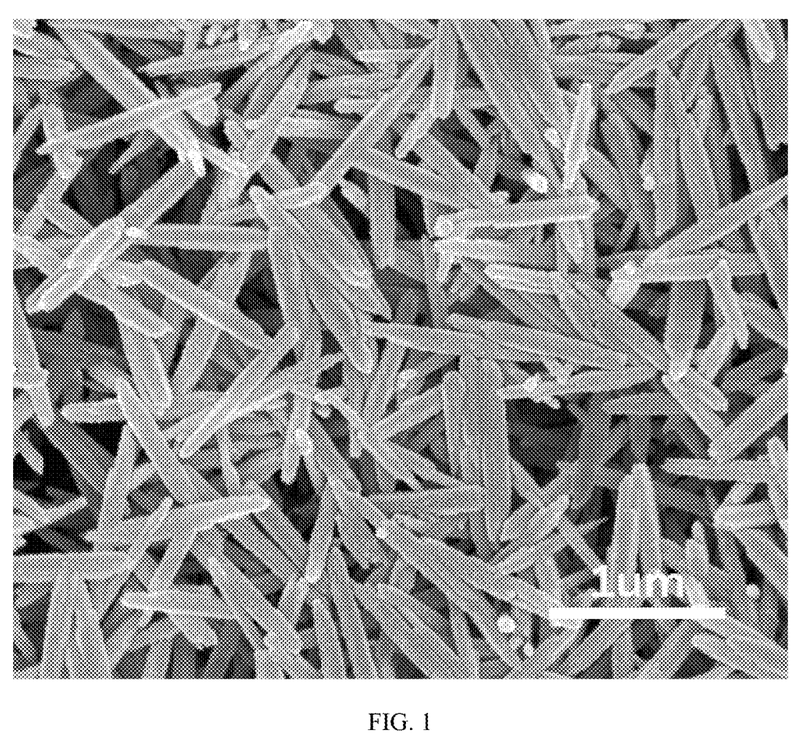
FIG. 1 is a scanning electron microscopy (SEM) image of a selenium-doped hydroxyapatite obtained in Example 1.
Figure 2:
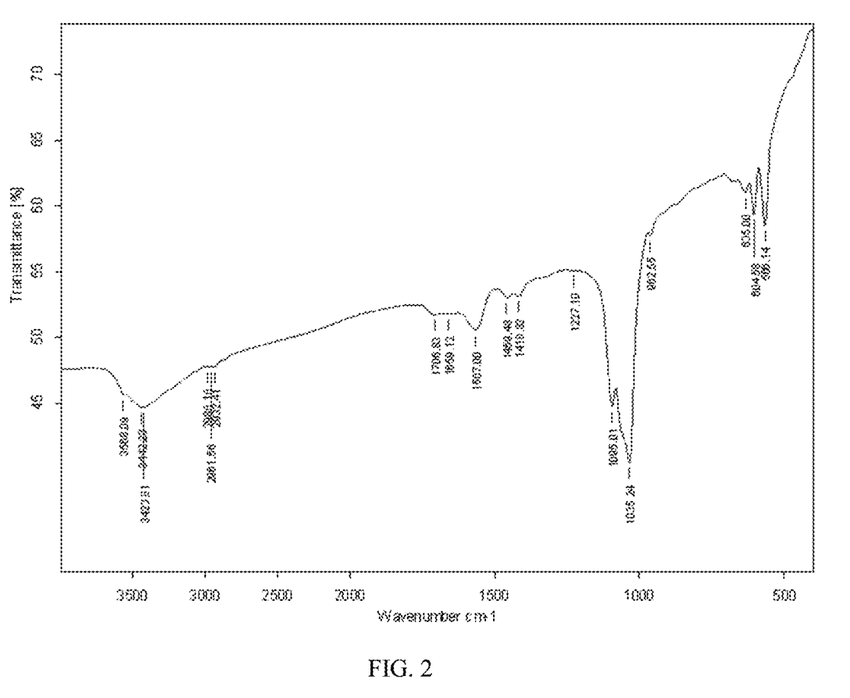
FIG. 2 is an infrared (IR) spectrum of the selenium-doped hydroxyapatite obtained in Example 1.
Figure 3:
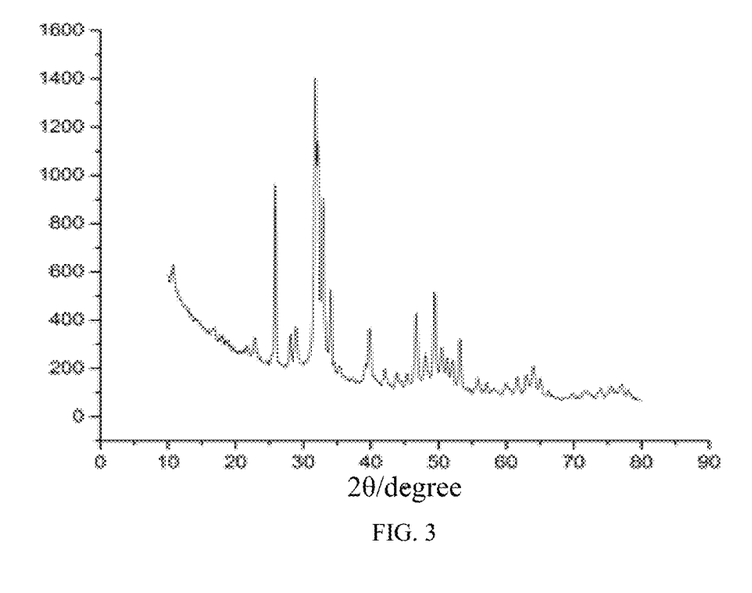
FIG. 3 is an X-ray diffraction pattern of the selenium-doped hydroxyapatite obtained in Example 1.
Figure 4:
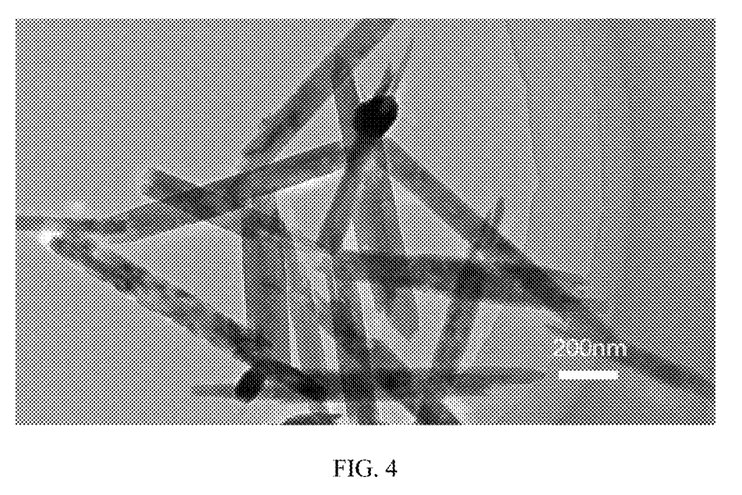
FIG. 4 is a transmission electron microscopy (TEM) image of the selenium-doped hydroxyapatite obtained in Example 1.
Figure 5:
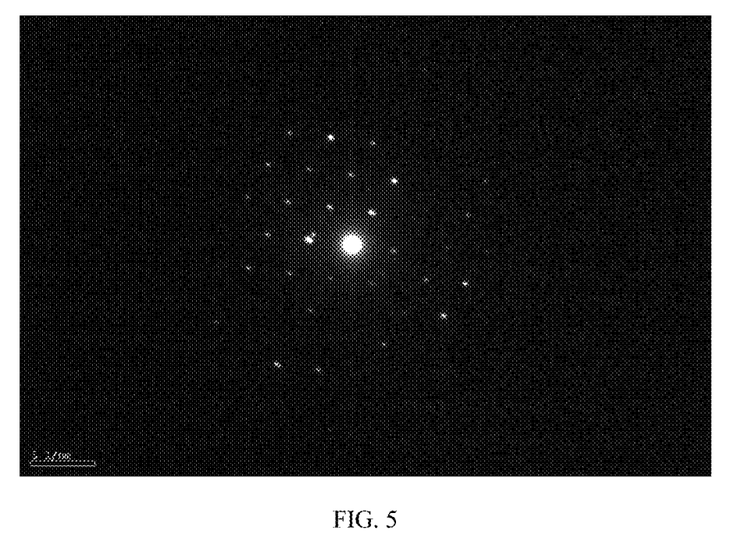
FIG. 5 is an electron diffraction pattern of the selenium-doped hydroxyapatite obtained in Example 1.
Figure 9:
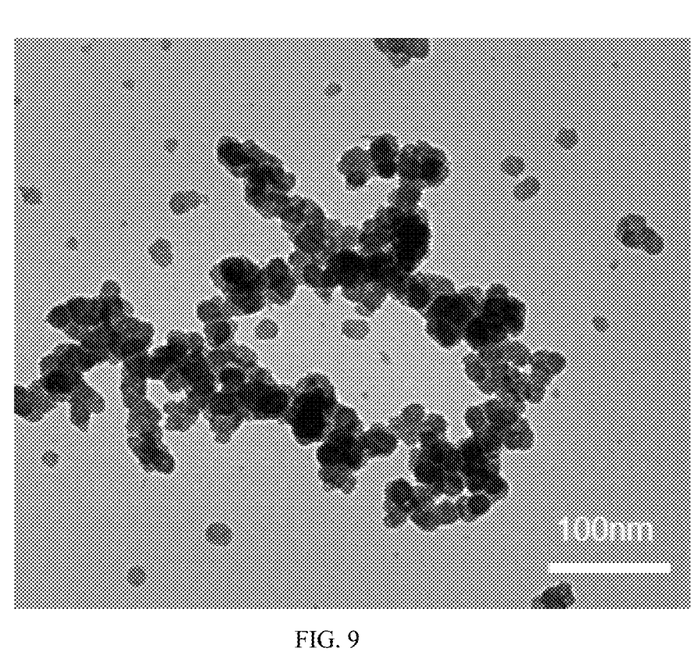
FIG. 9 is a TEM image of a calcium phosphate amorphous precursor obtained in Example 1.

FIG. 9 is a TEM image of the amorphous calcium phosphate precursor, showing that the amorphous calcium phosphate precursor is spherical. FIG. 1 is a SEM image of the selenium-doped hydroxyapatite, showing that the prepared material is of a rod-like shape having a width of about 120 nm and a length of about 1 μm. FIG. 2 is an IR spectrum of the granular material, it clearly shown that the reaction product comprises hydroxyl group, methyl group, phosphate, and selenium-oxygen bond. In combination with the X-ray diffraction pattern (FIG. 3), it can be seen that the reaction product obtained in the present invention is a selenium-doped hydroxyapatite. FIG. 4 is a TEM image of the prepared material showing that the prepared material is of a rod-like shape having a width of about 110 run and a length of about 1 μm. FIG. 5 is an electron diffraction pattern of the prepared material, showing that the resulting product has a single crystal structure.

Example 2

By the following preparation method, a hydroxyapatite doped with selenium in an amount of 6% was synthesized. The steps were specifically as follows.

(1) 2.95 g of calcium nitrate was dissolved in 250 mL of water, and 0.825 g of ammonium dihydrogen phosphate and 0.311 g of sodium selenite were dissolved in 250 mL of water, and stirred at room temperature until they were completely dissolved, to obtain a solution of a calcium nitrate and a mixed solution of an ammonium dihydrogen phosphate and a sodium selenite, respectively.

(2) The solution of the calcium nitrate was warmed to a temperature of 85° C. in a constant-temperature magnetic stirrer, and adjusted to pH 10 with aqueous ammonia. 2 mL of a solution of sodium polyacrylate was added dropwise to the solution of the calcium nitrate to obtain a mixed solution of a calcium nitrate and a sodium polyacrylate. The mixed solution of the ammonium dihydrogen phosphate and the sodium selenite was slowly added dropwise to the mixed solution of the calcium nitrate and the sodium polyacrylate, duration of the dropwise process is 30 min.

(3) The reaction solution was maintained at pH 10 by adding aqueous ammonia dropwise, the temperature was maintained at 85° C. by the constant-temperature magnetic stirrer, and the reaction was continued for 2 hrs.

(4) The reaction solution was centrifuged, and a precipitate of an amorphous calcium phosphate precursor was collected. 50 mL of anhydrous ethanol was added to the precipitate of the amorphous calcium phosphate precursor, transferred to a reactor, sealed, and reacted for 24 hrs at a temperature maintained at 190° C.

(5) After naturally cooling to room temperature, the reactor was opened, and a selenium-doped hydroxyapatite was finally obtained after several rounds of sequential washing with anhydrous ethanol and water, and drying.

Figure 6:
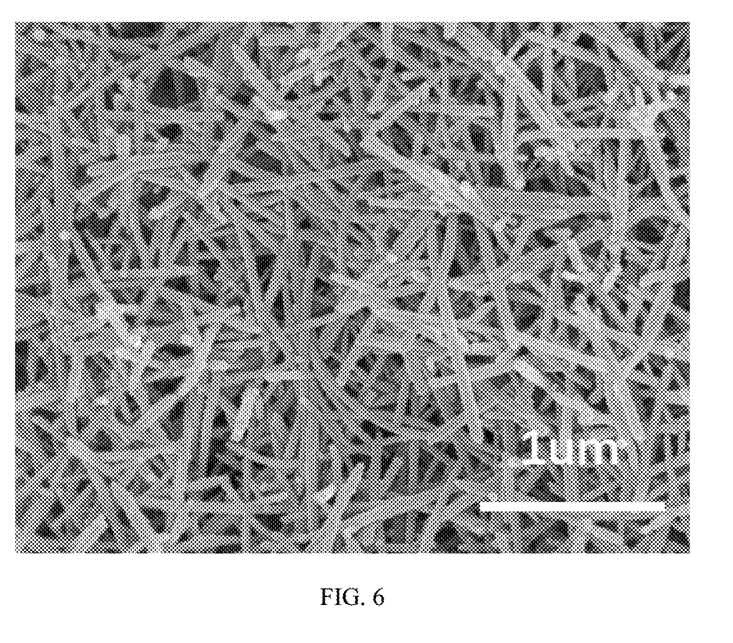
FIG. 6 is an SEM image of a selenium-doped hydroxyapatite obtained in Example 2.

FIG. 6 is a SEM image of the selenium-doped hydroxyapatite, showing that the prepared material is of a rod-like shape having a width of about 40 nm and a length of about 1.1 μm.

Example 3

By the following preparation method, a hydroxyapatite doped with selenium in an amount of 0.5% was synthesized. The steps were specifically as follows.

(1) 2.95 g of calcium nitrate was dissolved in 250 mL of water, and 0.952 g of ammonium dihydrogen phosphate and 0.075 g of sodium selenite were dissolved in 250 mL of water, and stirred at room temperature until they were completely dissolved, to obtain a solution of a calcium nitrate and a mixed solution of an ammonium dihydrogen phosphate and a sodium selenite, respectively.

(2) The solution of the calcium nitrate was warmed to a temperature of 80° C. in a constant-temperature magnetic stirrer, and adjusted to pH 10 with aqueous ammonia. 1 mL of a solution of sodium polyacrylate was added dropwise to the solution of the calcium nitrate to obtain a mixed solution of a calcium nitrate and a sodium polyacrylate. The mixed solution of the ammonium dihydrogen phosphate and the sodium selenite was slowly added dropwise to the mixed solution of the calcium nitrate and the sodium polyacrylate, duration of the dropwise process is 30 min.

(3) The reaction solution was maintained at pH 10 by adding aqueous ammonia dropwise, the temperature was maintained at 80° C. by the constant-temperature magnetic stirrer, and the reaction was continued for 2.5 hrs.

(4) The reaction solution was centrifuged, and a precipitate of an amorphous calcium phosphate precursor was collected. 50 mL of anhydrous ethanol was added to the precipitate of the amorphous calcium phosphate precursor, transferred to a reactor, sealed, and reacted for 24 hrs at a temperature maintained at 190° C.

(5) After naturally cooling to room temperature, the reactor was opened, and a selenium-doped hydroxyapatite was finally obtained after several rounds of sequential washing with anhydrous ethanol and water, and drying.

The obtained selenium-doped hydroxyapatite is of a rod-like shape having a width of about 80 nm and a length of about 1 μm, and having a good dispersibility and a single crystal structure.

Example 4

By the following preparation method, a hydroxyapatite doped with selenium in an amount of 6% was synthesized. The steps were specifically as follows.

(1) 2.95 g of calcium nitrate was dissolved in 250 mL of water, and 0.825 g of ammonium dihydrogen phosphate and 0.311 g of sodium selenite were dissolved in 250 mL of water, and stirred at room temperature until they were completely dissolved, to obtain a solution of a calcium nitrate and a mixed solution of an ammonium dihydrogen phosphate and a sodium selenite, respectively.

(2) The solution of the calcium nitrate was warmed to a temperature of 90° C. in a constant-temperature magnetic stirrer, and adjusted to pH 9 with aqueous ammonia. 2 mL of a solution of sodium polyacrylate was added dropwise to the solution of the calcium nitrate to obtain a mixed solution of a calcium nitrate and a sodium polyacrylate. The mixed solution of the ammonium dihydrogen phosphate and the sodium selenite was slowly added dropwise to the mixed solution of the calcium nitrate and the sodium polyacrylate, duration of the dropwise process is 30 min.

(3) The reaction solution was maintained at pH 9 by adding aqueous ammonia dropwise, the temperature was maintained at 90° C. by the constant-temperature magnetic stirrer, and the reaction was continued for 1.5 hrs.

(4) The reaction solution was centrifuged, and a precipitate of an amorphous calcium phosphate precursor was collected. 50 mL of anhydrous ethanol was added to the precipitate of the amorphous calcium phosphate precursor, transferred to a reactor, sealed, and reacted for 16 hrs at a temperature maintained at 210° C.

(5) After naturally cooling to room temperature, the reactor was opened, and a selenium-doped hydroxyapatite was finally obtained after several rounds of sequential washing with anhydrous ethanol and water, and drying.

The obtained selenium-doped hydroxyapatite is of a rod-like shape having a width of about 50 nm and a length of about 1.1 μm, and having a good dispersibility and a single crystal structure.

Comparative Example 1

(1) 2.95 g of calcium nitrate was dissolved in 250 mL of water, and 0.93 g of ammonium dihydrogen phosphate and 0.12 g of sodium selenite were dissolved in 250 mL of water, and stirred at room temperature until they were completely dissolved, to obtain a solution of a calcium nitrate and a mixed solution of an ammonium dihydrogen phosphate and a sodium selenite, respectively.

(2) The solution of the calcium nitrate was warmed to a temperature of 85° C. in a constant-temperature magnetic stirrer, and adjusted to pH 9 with aqueous ammonia. 1 mL of a solution of 50% sodium polyacrylate was added dropwise to the solution of the calcium nitrate to obtain a mixed solution of a calcium nitrate and a sodium polyacrylate. The mixed solution of the ammonium dihydrogen phosphate and the sodium selenite was slowly added dropwise to the mixed solution of the calcium nitrate and the sodium polyacrylate, and duration of the dropwise process is 30 min.

(3) The reaction solution was maintained at pH 9 by adding aqueous ammonia dropwise, the temperature was maintained at 85° C. by the constant-temperature magnetic stirrer, and the reaction was continued for 1 hr.

(4) The reaction solution was centrifuged, and a precipitate of an amorphous calcium phosphate precursor was collected. 50 mL of anhydrous ethanol was added to the precipitate of the amorphous calcium phosphate precursor, transferred to a reactor, sealed, and reacted for 24 hrs at a temperature maintained at 200° C.

(5) After naturally cooling to room temperature, the reactor was opened, and a selenium-doped hydroxyapatite was finally obtained after several rounds of sequential washing with anhydrous ethanol and water, and drying.

Figure 7:
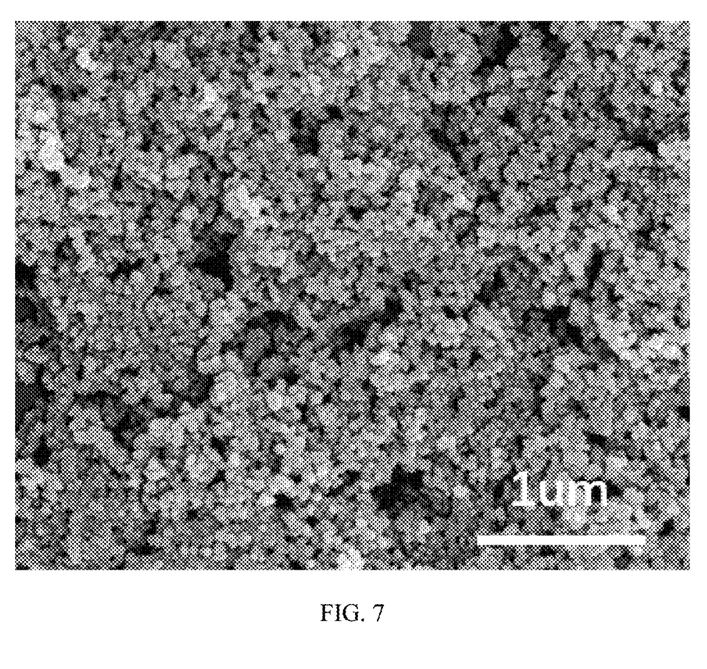
FIG. 7 is an SEM image of a selenium-doped hydroxyapatite obtained in Comparative Example 1

FIG. 7 is a SEM image of the selenium-doped hydroxyapatite, showing that the material thus prepared has a granular morphology, and has severe agglomeration and poor dispersibility.

Comparative Example 2

(1) 2.95 g of calcium nitrate was dissolved in 250 mL of water, and 0.825 g of ammonium dihydrogen phosphate and 0.311 g of sodium selenite were dissolved in 250 mL of water, and stirred at room temperature until they were completely dissolved, to obtain a solution of a calcium nitrate and a mixed solution of an ammonium dihydrogen phosphate and a sodium selenite, respectively.

(2) The solution of the calcium nitrate was warmed to a temperature of 85° C. in a constant-temperature magnetic stirrer, and adjusted to pH 10 with aqueous ammonia. 2 mL of a solution of sodium polyacrylate was added dropwise to the solution of the calcium nitrate to obtain a mixed solution of a calcium nitrate and a sodium polyacrylate. The mixed solution of the ammonium dihydrogen phosphate and the sodium selenite was slowly added dropwise to the mixed solution of the calcium nitrate and the sodium polyacrylate, and duration of the dropwise process is 30 min.

(3) The reaction solution was maintained at pH 10 by adding aqueous ammonia dropwise, the temperature was maintained at 85° C. by the constant-temperature magnetic stirrer, and the reaction was continued for 3 hrs.

(4) The reaction solution was centrifuged, and a precipitate of an amorphous calcium phosphate precursor was collected. 50 mL of anhydrous ethanol was added to the precipitate of the amorphous calcium phosphate precursor, transferred to a reactor, sealed, and reacted for 24 hrs at a temperature maintained at 190° C.

(5) After naturally cooling to room temperature, the reactor was opened, and a selenium-doped hydroxyapatite was finally obtained after several rounds of sequential washing with anhydrous ethanol and water, and drying.

Figure 8:
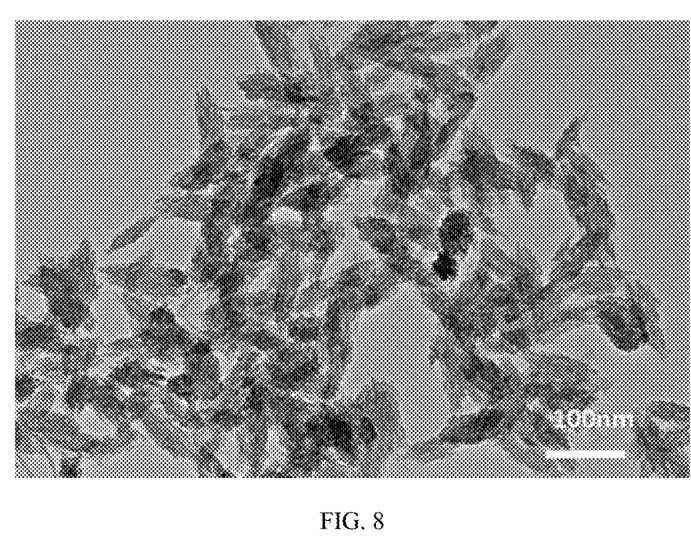
FIG. 8 is a TEM image of a selenium-doped hydroxyapatite obtained in Comparative Example 2

FIG. 8 is a TEM image of the selenium-doped hydroxyapatite, showing that the material thus prepared has a fusiform-like morphology having a length of about 100 nm and a width of about 30 nm, and has poor dispersibility.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A method for preparing a selenium-doped hydroxyapatite, comprising: adding a mixed solution of a phosphate and a selenite dropwise to a mixed solution of a calcium salt and a dispersing agent, and reacting for 1.5-2.5 hrs at a controlled temperature of 80-90° C., to obtain a solution of a calcium phosphate amorphous precursor, followed by performing a hydrothermal reaction at 190-210° C. for 12-24 hrs, to obtain a selenium-doped hydroxyapatite with a rod-like single crystal structure, which has a uniform morphology and a good dispersibility, wherein the selenium-doped hydroxyapatite comprises a diameter ranging from 30 nm to 300 nm, and a length ranging from 500 nm to 2 μm.

2. The method according to claim 1, comprising steps of:
(1) adding the mixed solution of the phosphate and the selenite dropwise to the mixed solution of the calcium salt and the dispersing agent, and reacting for 1.5-2.5 hrs at pH 9-10 and at a reaction temperature of 80-90° C., to obtain a solution of an amorphous calcium phosphate precursor;
(2) centrifuging the solution of the amorphous calcium phosphate precursor, collecting a precipitate of an amorphous calcium phosphate precursor, adding anhydrous ethanol, placing in a reactor, and reacting for 12-24 hrs at a temperature maintained at 190-210° C.; and
(3) washing the precipitate of the amorphous calcium phosphate precursor with anhydrous ethanol and water respectively, and centrifuging, to remove the impurity ions in the post-reaction system, and drying, to finally obtain the selenium-doped hydroxyapatite comprising a rod-like structure.

3. The method according to claim 1, wherein a molar ratio of the elements calcium, phosphorous and selenium is 1:(0.42-0.58):(0.17-0.006).

4. The method according to claim 1, wherein the calcium salt is calcium nitrate, the phosphate is ammonium dihydrogen phosphate, dibasic sodium phosphate or dibasic ammonium phosphate, and the selenite is sodium selenite.

5. The method according to claim 1, wherein the dispersing agent is sodium polyacrylate.

* * * * *